United States Patent
Lüpke et al.

(10) Patent No.: US 8,450,113 B2
(45) Date of Patent: May 28, 2013

(54) CONTAINER PRODUCTION METHOD AND DEVICE PROVIDING CONTAINER WALL SURFACE COATING AND DETERMINING WALL GAS PERMEABILITY OF RANDOMLY SELECTED CONTAINERS

(75) Inventors: Erik Lüpke, Hamburg (DE); Klaus Hartwig, Hamburg (DE)

(73) Assignee: KHS Corpoplast GmbH & Co. KG, Hamburg (DE)

( * ) Notice: Subject to any disclaimer, the term of this patent is extended or adjusted under 35 U.S.C. 154(b) by 714 days.

(21) Appl. No.: 10/580,386

(22) PCT Filed: Oct. 12, 2004

(86) PCT No.: PCT/DE2004/002263
§ 371 (c)(1),
(2), (4) Date: Jan. 16, 2007

(87) PCT Pub. No.: WO2005/052555
PCT Pub. Date: Jun. 9, 2005

(65) Prior Publication Data
US 2007/0215046 A1 Sep. 20, 2007

(30) Foreign Application Priority Data
Nov. 22, 2003 (DE) .................................. 103 54 625

(51) Int. Cl.
*G01N 15/08* (2006.01)
*G01N 7/14* (2006.01)

(52) U.S. Cl.
USPC ............................ 436/5; 73/38; 436/2; 436/3

(58) Field of Classification Search
USPC ............................................. 73/38; 436/2–3, 5
See application file for complete search history.

(56) References Cited

U.S. PATENT DOCUMENTS

| 3,286,509 | A | * | 11/1966 | Gluckman et al. | 73/38 |
| 3,352,146 | A | * | 11/1967 | Lyssy | 73/38 |
| 3,572,096 | A | * | 3/1971 | Meyer | 73/40.7 |
| 3,604,246 | A | * | 9/1971 | Toren | 73/38 |
| 3,902,068 | A | * | 8/1975 | Wood | 250/343 |
| 4,047,422 | A | * | 9/1977 | Lyssy | 73/38 |
| 4,112,739 | A | * | 9/1978 | Lyssy | 73/38 |
| 4,391,128 | A | | 7/1983 | McWhorter | |
| 4,464,927 | A | * | 8/1984 | Reid | 73/38 |
| 4,468,951 | A | * | 9/1984 | Garcia et al. | 73/38 |

(Continued)

FOREIGN PATENT DOCUMENTS

| DE | 199 46 080 | 5/2000 |
| DE | 101 24 225 | 1/2003 |

(Continued)

*Primary Examiner* — Arlen Soderquist
(74) *Attorney, Agent, or Firm* — Lucas & Mercanti, LLP; Klaus P. Stoffel

(57) ABSTRACT

The invention relates to a method and a device for determining the gas permeability of barrier coatings (1) in the region of container walls (2). A quantity of gas to be analyzed emerging from the region of the wall of the container into an analysis chamber that is at least partially defined by the barrier coating is measured in said analysis chamber (8). Before entering the analysis chamber, the gas to be analyzed is located in the region of the wall. The measuring element can be integrated into a coating device for the container. To this end, a testing device provided with the measuring element is arranged in the transport direction of the container behind the coating device.

18 Claims, 2 Drawing Sheets

U.S. PATENT DOCUMENTS

| | | | |
|---|---|---|---|
| 4,656,865 A * | 4/1987 | Callan | 73/38 |
| 4,659,674 A * | 4/1987 | Bauman et al. | 436/5 |
| 4,858,767 A * | 8/1989 | Myers et al. | 209/3.1 |
| 5,107,696 A * | 4/1992 | Mayer et al. | 73/38 |
| 5,265,463 A * | 11/1993 | Loebig | 73/38 |
| 5,361,625 A * | 11/1994 | Ylvisaker | 73/38 |
| 5,378,510 A * | 1/1995 | Thomas et al. | 427/563 |
| 5,381,228 A * | 1/1995 | Brace | 356/300 |
| 5,390,539 A * | 2/1995 | Mayer | 73/38 |
| 5,483,819 A | 1/1996 | Barmore et al. | |
| 5,513,515 A * | 5/1996 | Mayer | 73/38 |
| 5,521,351 A * | 5/1996 | Mahoney | 219/121.59 |
| 5,531,060 A * | 7/1996 | Fayet et al. | 53/426 |
| 5,565,248 A * | 10/1996 | Plester et al. | 427/571 |
| 5,591,898 A * | 1/1997 | Mayer | 73/38 |
| 5,679,412 A * | 10/1997 | Kuehnle et al. | 427/534 |
| 5,792,940 A * | 8/1998 | Ghandhi | 73/40 |
| 5,800,880 A | 9/1998 | Laurent | 427/583 |
| 5,849,366 A * | 12/1998 | Plester | 427/491 |
| 6,009,743 A * | 1/2000 | Mayer | 73/38 |
| 6,050,133 A | 4/2000 | Achter et al. | |
| 6,112,695 A * | 9/2000 | Felts | 118/723 E |
| 6,149,982 A * | 11/2000 | Plester | 427/491 |
| 6,223,683 B1 * | 5/2001 | Plester et al. | 118/723 VE |
| 6,242,053 B1 * | 6/2001 | Anderle et al. | 427/488 |
| 6,251,233 B1 * | 6/2001 | Plester et al. | 204/192.38 |
| 6,276,296 B1 * | 8/2001 | Plester | 118/723 R |
| 6,376,028 B1 * | 4/2002 | Laurent et al. | 427/571 |
| 6,640,615 B1 * | 11/2003 | Morrow | 73/38 |
| 6,964,191 B1 * | 11/2005 | Tata | 73/38 |
| 7,121,135 B2 * | 10/2006 | Moore | 73/38 |
| 7,624,622 B1 * | 12/2009 | Mayer et al. | 73/38 |
| 2002/0134934 A1 * | 9/2002 | Haney et al. | 250/288 |
| 2002/0162384 A1 * | 11/2002 | Sharp et al. | 73/38 |
| 2002/0173040 A1 | 11/2002 | Potyrailo et al. | |
| 2002/0194899 A1 * | 12/2002 | Gebele et al. | 73/38 |
| 2003/0046982 A1 * | 3/2003 | Chatard | 73/38 |
| 2003/0087030 A1 * | 5/2003 | Hama et al. | 427/209 |
| 2004/0040372 A1 * | 3/2004 | Plester et al. | 73/38 |
| 2004/0177676 A1 * | 9/2004 | Moore | 73/38 |
| 2006/0110483 A1 * | 5/2006 | Damerow et al. | 425/1 |
| 2006/0169026 A1 * | 8/2006 | Kage et al. | 73/38 |
| 2006/0177575 A1 * | 8/2006 | Takemoto et al. | 427/248.1 |

FOREIGN PATENT DOCUMENTS

| | | |
|---|---|---|
| GB | 2 078 662 | 1/1982 |
| WO | 01/48452 | 7/2001 |
| WO | 02/059557 | 8/2002 |

\* cited by examiner

CONTAINER PRODUCTION METHOD AND DEVICE PROVIDING CONTAINER WALL SURFACE COATING AND DETERMINING WALL GAS PERMEABILITY OF RANDOMLY SELECTED CONTAINERS

The invention concerns a method for determining the gas permeability of the walls of a container, which is furnished with a barrier coating at least in the area of a first surface of the walls.

The invention also concerns a container made of a thermoplastic, which is furnished with a barrier coating at least in the area of a first surface of its walls to improve its gas barrier properties.

Finally, the invention concerns a device for coating containers, which has a coating device for at least partially coating at least part of a surface of the container with a coating substance.

Many of the previously known methods and devices for determining the gas permeability of container walls, especially for determining the gas permeability of containers made of a thermoplastic, have the disadvantage that a considerable amount of time is required to make the determination. In connection with the measurement of the gas permeability of the walls of PET bottles, methods are known, for example those described in the German standard DIN 53380, which require a typical measuring time of 5 to 7 days. Although methods of this type are suitable for obtaining basic information with respect to the usefulness of certain methods or with respect to the material properties of certain wall designs, the previously known methods and devices are not suitable for continuous use for production monitoring with early detection of production problems. Measuring methods involving the use of hydrogen peroxide are also known, but they are imprecise and are not operator-friendly.

DE 101 24 225 A1 describes a method for measuring the barrier properties relatively quickly. However, a disadvantage of this method is that the measurement requires that a negative pressure be created inside the container. This results in increased equipment expense and makes it especially difficult to integrate the measuring method in a production monitoring system.

A large number of methods are already known for reducing the gas permeability of the walls of thermoplastic containers. In the meantime, wide use has been found for a multilayer wall structure in which typically a middle wall layer has a high gas barrier effect. It is also well known that certain copolymers, whose molecular structure provides a relatively dense microstructure, can be used to prevent the permeation of gas. It is also known that so-called sacrificial substances can be incorporated in the material of the walls to adsorb the penetrating gas particles and thus prevent their permeation.

In accordance with other well-known methods, increased gas impermeability is achieved in the blow molding of thermoplastic containers by means of special stretching conditions, temperature conditioning, and blowing pressure variations. Finally, it is also already known that the inner and/or outer surfaces of the container walls can be furnished with special coatings. Coatings of this type have recently also been produced by plasma technologies.

Regardless of the actual practical realization of increased gas impermeability of the given container walls, the previously known methods and devices for determining the gas impermeability cannot yet meet all of the requirements for fast performance of the measurement, high measurement accuracy, and sufficient sensitivity to disturbances.

The objective of the present invention is to improve a method of the aforementioned type in such a way that the speed of the analysis is increased and a high degree of analytical quality is achieved at the same time.

In accordance with the invention, this objective is achieved by measuring a concentration of an analytical gas in an analytical space that is at least partially bounded by the barrier coating, which analytical gas escapes from the area of the container wall into the analytical space and which was bound in the area of the container wall before its escape into the analytical space.

A further objective of the present invention is to design a container of the aforementioned type in a way that is conducive to rapid performance of the analysis.

In accordance with the invention, this objective is achieved by arranging an analytical substance in the area of the surface of the wall that faces the barrier coating, which analytical substance at least temporarily releases an analytical gas.

An additional objective of the present invention is to design a device for coating containers of the aforementioned type in a way that is conducive to monitoring production quality.

In accordance with the invention, this objective is achieved by arranging a testing device for measuring the coating quality of at least some of the containers downstream of the coating device in the direction of conveyance of the containers.

By using as the analytical gas a substance that is loosely bound in the area of the container wall in such a way that escape from the container wall is possible, a substance that can be used for the analysis is already made available directly below the barrier coating immediately after completion of the coating operation. Accordingly, after the coating operation has been carried out, it is not necessary first to expose the coated container to an environment that contains the analytical gas and then wait for saturation of the material of the container with the analytical gas. This saturation time, which is typically 30-60 minutes, can be avoided by the immediate presence of the analytical substance in the area of the container wall. Analysis times on the order of a few minutes can be realized in this way. In the discussion which follows, the container wall whose gas permeability is to be determined is understood to mean the combination of the actual wall and the barrier coating.

It is conducive to a very high quality of measurement if fractions of the analytical gas are measured in a space that contains practically no analytical gas before the start of the measurement. This makes it possible to realize very high measurement sensitivity even with relatively small amounts of the substance to be detected.

Due to the chosen measuring principle, a very compact design of the device can be realized. It is also possible to achieve a very low sensitivity of both the measuring method and the measuring device to disturbances in order to help achieve stably high production quality when the measuring device is integrated in a device for coating containers.

In a variant of the method that is technically simple to realize, the analytical gas is physically bound in the area of the wall.

It is also feasible for the analytical gas to be chemically bound in the area of the wall.

A relatively large amount of analytical substance can be made available by binding the analytical gas within the wall.

Binding the analytical gas in an intermediate layer between the wall and the barrier coating is especially conducive to the achievement of very short measurement times.

A reduction of the analytical substance by storage of the container before it is coated is avoided by binding the analytical gas in an area of the barrier coating that faces the wall.

It is conducive to performance of the method that is simple from the standpoint of measurement technology if the measurement of the analytical gas is carried out at a pressure that is selected to be essentially the same as ambient pressure.

It is also conducive to simple performance of the method if water vapor is used as the analytical gas.

The use of oxygen as the analytical gas is also feasible.

In accordance with another embodiment, it is also possible to use nitrogen as the analytical gas.

The method can also be carried out with the use of carbon dioxide as the analytical gas.

One variant for the introduction of the analytical substance into the material of the container wall is characterized by the fact that, to bind the analytical gas in the area of the wall, the containers are preconditioned before the coating operation is carried out. It is also possible to perform the preconditioning after the coating operation and before the measurement is carried out.

Flexible performance of the measuring method can be achieved by carrying out a measurement of the analytical gas in a carrier gas.

A barrier measurement after the containers are filled can be carried out by performing a measurement of the analytical gas in a carrier liquid.

To help achieve high measurement accuracy, it is proposed that the measurement space be preconditioned in such a way before the measurement is made that it contains essentially no analytical gas.

In the case of containers with an inner coating, it has been found to be advantageous to measure the analytical gas in an interior cavity of the container.

In the case of containers with an outer coating, it is advantageous to measure the analytical gas in a reference space that surrounds the container.

To help integrate the testing device in the coating device, the testing device is coupled with a control unit for the coating device.

In a typical embodiment, the coating device is designed for coating the containers on the inside.

It is also possible to design the coating device to coat the containers on the outside.

In accordance with another embodiment, it is also possible for the coating device to be designed for plasma coating of the containers.

Specific embodiments of the invention are schematically illustrated in the drawings.

Figure 1:
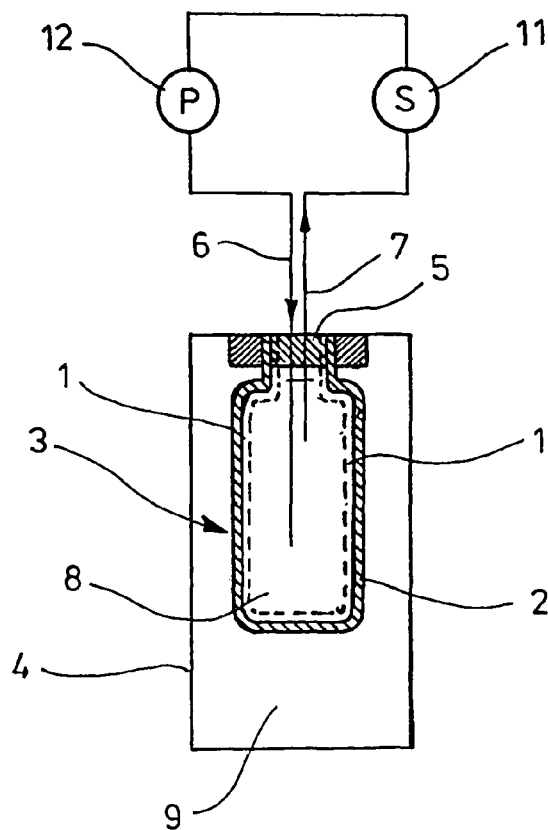
FIG. 1 shows a schematic representation of the measuring device.

FIG. 1 shows a device for determining the gas permeability of a barrier coating 1 of walls 2 of a container 3. The container 3 is mounted in a mounting device 4, which at least partially encloses the container 3. The mounting device 4 has a mouth closure 5 for the container 3 with an inlet 6 and an outlet 7 for a carrier gas. In the illustrated embodiment, the carrier gas is introduced into an interior cavity 8 of the container 3. This allows the carrier gas to come into contact with the barrier coating 1 of the container 3. In the illustrated embodiment, the barrier coating 1 is arranged facing the interior cavity 8.

The carrier gas is introduced by a pump 10 into the interior cavity 8 through the inlet 6 and flows through the outlet 7 and past a sensor 11.

In the illustrated embodiment, a closed gas circulation is provided to save carrier gas. In principle, however, it is also possible to use an open system. Before the measuring operation is carried out, the interior cavity 8 is typically flushed with carrier gas to produce well-defined initial conditions.

In an embodiment in which the barrier coating 1 is furnished on the outside of the container 3, the mounting device 6 is designed as a closed chamber with a reference space 9, into which the container 3 is inserted. In this case, the inlet 6 and the outlet 7 open into the reference space 9, so that the carrier gas flows around the barrier coating 1, which has been applied to the outer surface of the container. Otherwise, however, a comparable measurement principle is realized.

Both when the barrier coating 1 is applied to the inner surface of the wall 2 and when it is applied to the outer surface of the wall, the sensor 11 detects fractions of an analytical gas in the carrier gas. The analytical gas passes through the barrier coating 1 or escapes from the wall 2 in the area of uncoated surfaces of the wall. The substance that constitutes or releases the analytical gas can already be incorporated in the wall 2 during the production of the containers 3. In the case of blow molding of the containers 3, it is possible, for one thing, to already introduce the given substance into the material during a preceding injection-molding operation for producing preforms, which are later molded into containers 3. It is also possible to deposit the substance on a surface of the wall 2 during or after the blow molding of the preforms into containers 3. Finally, it is also possible to deposit the given substance on the wall 2 shortly before the barrier coating 1 is applied. This can be done either in a separate process step or in a first coating step during the production of a multilayer coating or a gradient coating.

In particular, it is possible from the standpoint of process engineering to carry out the measurement of the analytical gas at ambient pressure without first generating a negative pressure in the measurement space. In a measurement space from which analytical gas has first been eliminated, the analytical gas escapes from the area of the wall 2 due to substance-specific partial-pressure differences, even when ambient pressure prevails.

Many different substances are suitable for use as the analytical gas. In the case of barrier measurements in the area of containers 3 that are intended for food packaging, it is proposed especially that the substances to be used are those which are approved in accordance with food safety laws. For example, it is possible first to introduce a dry gas, say, dry air, into the region of the measurement space and to detect the escape of water molecules from the area of the wall 2. It is likewise possible to measure the escape of oxygen or carbon dioxide from the area of the wall.

As an alternative to measurement of the analytical gas in a carrier gas, it is possible to perform the measurement in a carrier liquid. When the containers 3 are designed as bottles to be filled, it is proposed especially that a liquid that has previously been degassed with respect to the analytical gas be used as the carrier gas and that the measurement be carried out after the container 3 has been filled.

When containers 3 that are used are intended for the packaging of food, it is proposed especially that the wall 2 be made of PET or PEN and that the analytical substance be a material that is specially suited for adsorption on PET or PEN with optimum adsorption stability with respect to the required release of the substance.

In regard to the analytical substance, it is also proposed especially that substances be used which do not adversely affect the transparency of transparent walls 2 and do not cause unwanted discoloration of the wall 2.

Figure 2:
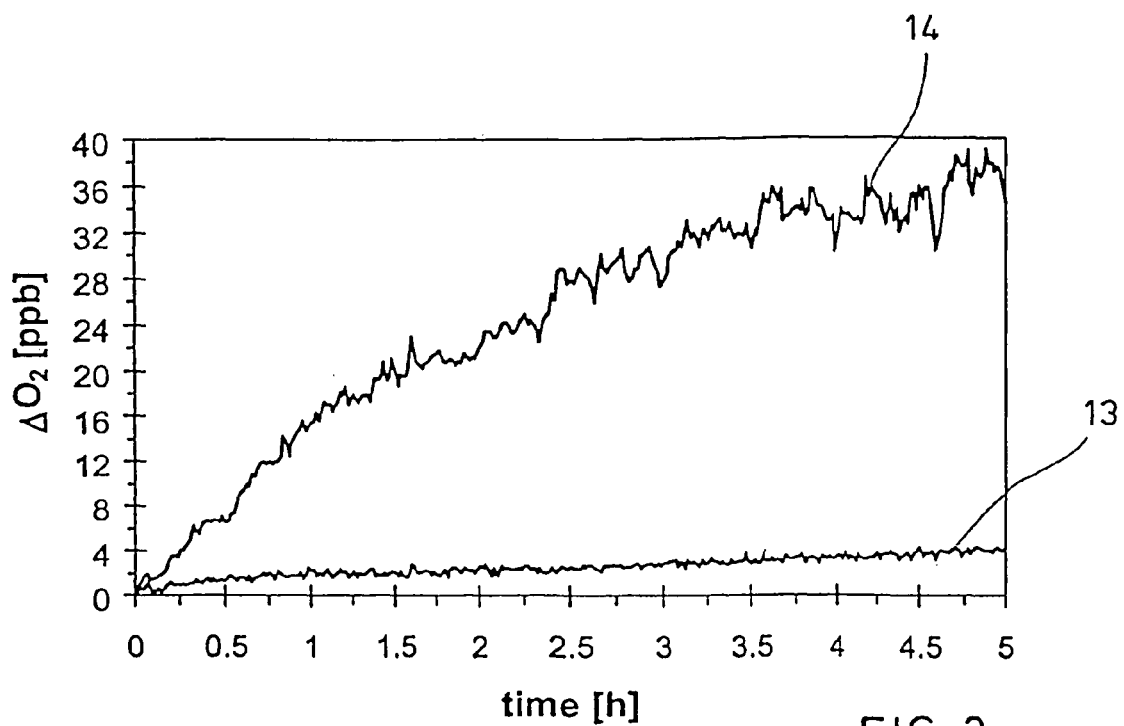
FIG. 2 shows a graph illustrating measurement results.

FIG. 2 shows a curve 13 of the escape of oxygen from the area of the wall 2 for a container 2 with a uniform and effective barrier coating 1 and a curve 14 for a container 3 without a barrier coating 1. It is apparent that even after only a few minutes, the curves 13, 14 diverge significantly.

Figure 3:
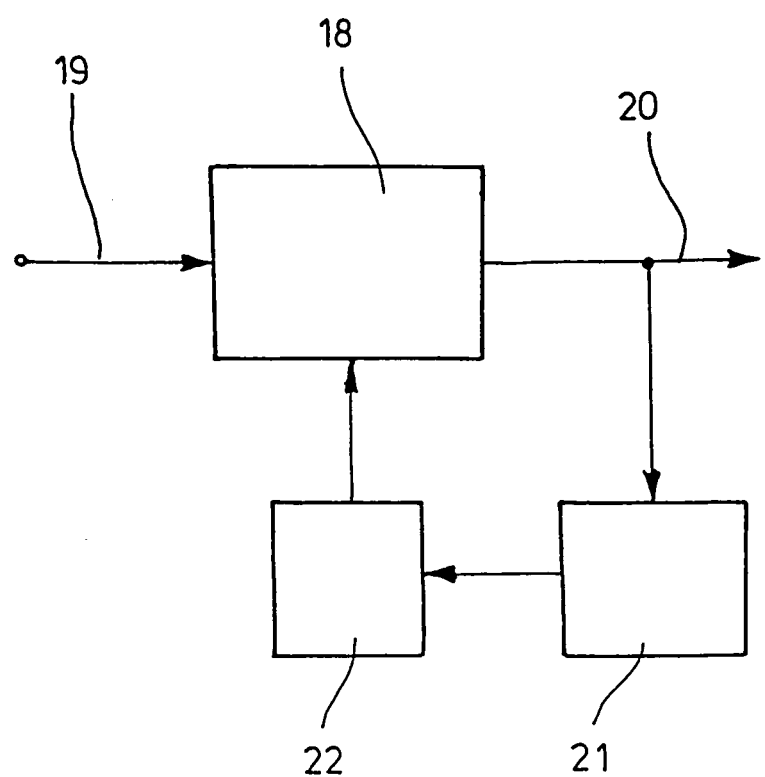
FIG. 3 shows a functional block diagram illustrating the integration of the measuring device in a device for coating containers.

FIG. 3 shows a coating device 18 for the containers 3, which has a container entrance 19 and a container exit 20. The container exit 20 is followed by a testing device 21, which comprises a mounting device 4 and a sensor 11. The testing device 21 is connected to a control unit 22 for the coating device 18 to carry out adjustments of machine settings as a function of the given measurement results and/or to produce a function display. For coating devices with high production counts per unit time, randomly sampled coated containers can be conveyed to the testing device 21 by controlled feeding. The control parameters of the control unit 22 can be adapted automatically or by user release.

The coating device can be designed for plasma coating of the containers 3. This is suitable especially for inside coating of the containers. $SiO_x$ can be used as the coating material, possibly with the use of adhesion promoters.

The invention claimed is:

1. A method for coating blow-molded containers, comprising the steps of:
    initially preconditioning each container by binding an analytical gas in the area of the wall;
    subsequently applying a barrier coating on an inner surface of the wall of the containers;
    randomly sampling some of the coated containers; and
    testing each of the sampled containers in a testing device for determining gas permeability of the walls of the containers, the testing including: measuring a concentration of analytical gas in an analytical space in an interior cavity of each of the sampled containers that is at least partially bounded by the barrier coating, which analytical gas escapes from the area of the wall of the container into the analytical space and which was bound in the area of the wall before its escape into the analytical space, the measurement of the analytical gas being carried out at a pressure that is selected to be substantially equal to ambient pressure so that there is no pressure difference between the interior of the container and the outside of the container; introducing a carrier gas so that the carrier gas flows through the interior cavity during measuring of the analytical gas; prior to the measuring, flushing the interior cavity with the carrier gas so that the analytical space is free of analytical gas; and, undertaking metrological determination of the analytical gas within the carrier gas so as to achieve analysis times on the order of a few minutes.

2. Method in accordance with claim 1, wherein the analytical gas is physically bound in the area of the wall (2).

3. Method in accordance with claim 1, wherein the analytical gas is chemically bound in the area of the wall (2).

4. Method in accordance with claim 1, wherein the analytical gas is bound within the wall (2).

5. Method in accordance with claim 1, wherein the analytical gas is bound in an intermediate layer between the wall (2) and the barrier coating (1).

6. Method in accordance with claim 1, wherein the analytical gas is bound in an area of the barrier coating (1) that faces the wall (2).

7. Method in accordance with claim 1, wherein water vapor is used as the analytical gas.

8. Method in accordance with claim 1, wherein oxygen is used as the analytical gas.

9. Method in accordance with claim 1, wherein nitrogen is used as the analytical gas.

10. Method in accordance with claim 1, wherein carbon dioxide is used as the analytical gas.

11. Method in accordance with claim 1, wherein the measurement of the analytical gas is carried out in a carrier liquid.

12. Method in accordance with claim 1, wherein the analytical substance is bound in the wall (2) in the form of a gas.

13. Method in accordance with claim 1, wherein the analytical substance is bound in the wall (2) in the form of a liquid.

14. Method in accordance with claim 1, wherein a carrier substance that releases the analytical substance is bound in the wall (2).

15. Method in accordance with claim 1, wherein the analytical substance is bound in a raw material for the production of the containers (2).

16. Method in accordance with claim 1, wherein the analytical substance is bound in an intermediate for the production of the containers (2).

17. Device for coating containers, which has a coating device for at least partially coating an inner surface of the container with a barrier coating, wherein a testing device (21) for measuring the coating quality of at least some of the containers (3) is arranged downstream of the coating device (18) in the direction of conveyance of the containers (3) and has a sensor (11) connected to an interior of the container (3) for the quantitative determination of an analytical gas escaping from the area of a wall (2) of the container (3), wherein the wall (2) of the container (3) contains the analysis gas prior to a production of the barrier, wherein the testing device (21) is coupled with a control unit (22) for the coating device (18), whereby an interior of the container is flushed with a carrier gas prior to the quantitative determination, and the carrier gas is introduced and flows through the interior cavity during the quantitative determination of the analytical gas, whereby the control unit is operative to produce a display and/or carry out adjustments of machine settings of the coating device as a function of measurements by the testing device.

18. Device in accordance with claim 17, wherein the coating device (18) is designed for plasma coating of the containers (3).

* * * * *

UNITED STATES PATENT AND TRADEMARK OFFICE
CERTIFICATE OF CORRECTION

PATENT NO. : 8,450,113 B2 Page 1 of 1
APPLICATION NO. : 10/580386
DATED : May 28, 2013
INVENTOR(S) : Lüpke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1063 days.

Signed and Sealed this
Eighth Day of September, 2015

Michelle K. Lee
*Director of the United States Patent and Trademark Office*